US010470495B2

(12) United States Patent
Sur et al.

(10) Patent No.: US 10,470,495 B2
(45) Date of Patent: Nov. 12, 2019

(54) LITHIUM-ION BATTERY WITH LINEAR REGULATION FOR AN AEROSOL DELIVERY DEVICE

(71) Applicant: RAI STRATEGIC HOLDINGS, INC., Winston-Salem, NC (US)

(72) Inventors: Rajesh Sur, Winston Salem, NC (US); Eric T. Hunt, Pfafftown, NC (US); Stephen B. Sears, Siler City, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 355 days.

(21) Appl. No.: 15/368,166

(22) Filed: Dec. 2, 2016

(65) Prior Publication Data
US 2017/0112195 A1    Apr. 27, 2017

Related U.S. Application Data

(63) Continuation-in-part of application No. 14/918,926, filed on Oct. 21, 2015.

(51) Int. Cl.
*A24F 47/00* (2006.01)
*H05B 1/02* (2006.01)
(Continued)

(52) U.S. Cl.
CPC .......... *A24F 47/008* (2013.01); *A24B 15/167* (2016.11); *A61M 11/042* (2014.02);
(Continued)

(58) Field of Classification Search
CPC ......... A24F 47/008; A24F 21/00; H05B 3/20; H05B 1/02; H05B 1/0244; H02J 7/0024; H02J 7/0047; H02J 7/0072; H02J 7/345
See application file for complete search history.

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

International Search Report dated Jan. 11, 2017 in International Application No. PCT/US2016/057293.

(Continued)

*Primary Examiner* — Brian W Jennison
(74) *Attorney, Agent, or Firm* — Womble Bond Dickinson (US) LLP

(57) ABSTRACT

An aerosol delivery device is provided that includes a reservoir configured to retain an aerosol precursor composition, a heating element, and a power source connected to an electrical load that includes the heating element. The power source includes a rechargeable lithium-ion battery and a linear regulator between the power source and load, the linear regulator being configured to maintain a constant voltage level at the electrical load. The aerosol delivery device also includes a microprocessor configured to operate in an active mode in which the microprocessor is configured to direct power from the power source to the heating element and thereby control the heating element to activate and vaporize components of the aerosol precursor composition.

12 Claims, 4 Drawing Sheets

(51) Int. Cl.
| | |
|---|---|
| *A24B 15/16* | (2006.01) |
| *H01G 11/06* | (2013.01) |
| *H01M 10/0525* | (2010.01) |
| *H01M 10/42* | (2006.01) |
| *H02J 7/00* | (2006.01) |
| *A61M 15/06* | (2006.01) |
| *A61M 11/04* | (2006.01) |
| *H02J 7/34* | (2006.01) |
| *A61M 16/00* | (2006.01) |

(52) U.S. Cl.
CPC ............ *A61M 15/06* (2013.01); *H01G 11/06* (2013.01); *H01M 10/0525* (2013.01); *H01M 10/4264* (2013.01); *H02J 7/007* (2013.01); *H02J 7/0065* (2013.01); *H02J 7/0068* (2013.01); *H05B 1/0244* (2013.01); *A61M 2016/0018* (2013.01); *A61M 2016/0027* (2013.01); *A61M 2016/0033* (2013.01); *A61M 2205/3368* (2013.01); *A61M 2205/3653* (2013.01); *A61M 2205/50* (2013.01); *A61M 2205/82* (2013.01); *A61M 2205/8206* (2013.01); *A61M 2205/8212* (2013.01); *A61M 2205/8262* (2013.01); *H01M 2220/30* (2013.01); *H02J 7/345* (2013.01); *H05B 2203/021* (2013.01)

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A * | 9/1992 | Counts .................. A24F 47/008 128/200.14 |
| 5,249,586 A | 10/1993 | Morgan et al. |
| 5,261,424 A | 11/1993 | Sprinkel, Jr. |
| 5,269,327 A * | 12/1993 | Counts .................. A24F 47/008 128/200.14 |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,528,569 B1 | 9/2013 | Newton |
| 8,550,069 B2 | 10/2013 | Alelov |
| 8,851,081 B2 | 10/2014 | Fernando et al. |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0067139 A1 | 3/2007 | Kobayashi |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 * | 9/2009 | Fernando .............. A24F 47/008 219/490 |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |

(56) References Cited

U.S. PATENT DOCUMENTS

| | | |
|---|---|---|
| 2011/0168194 A1 | 7/2011 | Hon |
| 2011/0265806 A1 | 11/2011 | Alarcon et al. |
| 2011/0309157 A1 | 12/2011 | Yang et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0227752 A1 | 9/2012 | Alelov |
| 2012/0231464 A1 | 9/2012 | Yu et al. |
| 2012/0260927 A1 | 10/2012 | Liu |
| 2012/0279512 A1 | 11/2012 | Hon |
| 2012/0318882 A1 | 12/2012 | Abehasera |
| 2013/0037041 A1 | 2/2013 | Worm et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0104916 A1 | 5/2013 | Bellinger |
| 2013/0192619 A1 | 8/2013 | Tucker et al. |
| 2013/0199528 A1 | 8/2013 | Goodman et al. |
| 2013/0243410 A1 | 9/2013 | Nichols et al. |
| 2013/0255702 A1 | 10/2013 | Griffith, Jr. et al. |
| 2013/0298905 A1* | 11/2013 | Levin .................. A24F 47/008 128/202.21 |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0014125 A1 | 1/2014 | Fernando et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0283855 A1 | 9/2014 | Hawes et al. |
| 2014/0299137 A1 | 10/2014 | Kieckbusch |
| 2014/0345631 A1 | 11/2014 | Bowen et al. |
| 2015/0007838 A1 | 1/2015 | Fernando et al. |
| 2015/0053217 A1 | 2/2015 | Steingraber et al. |
| 2016/0037826 A1 | 2/2016 | Hearn et al. |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 203 606 832 U | 5/2014 |
| DE | 10 2006 004 4 | 8/2007 |
| DE | 102006041042 | 3/2008 |
| DE | 20 2009 010 4 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 081 275 A1 | 7/2009 |
| EP | 2 100 525 A1 | 9/2009 |
| EP | 2 316 286 | 5/2011 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2012/072762 | 6/2012 |
| WO | WO 2012/100523 | 8/2012 |
| WO | 2012/120487 A2 | 9/2012 |
| WO | WO 2013/089551 | 6/2013 |
| WO | 2013/138384 A2 | 9/2013 |
| WO | 2016/118005 A1 | 7/2016 |

OTHER PUBLICATIONS

International Search Report dated Mar. 28, 2018; International Application No. PCT/IB2017/057469.

* cited by examiner

LITHIUM-ION BATTERY WITH LINEAR REGULATION FOR AN AEROSOL DELIVERY DEVICE

TECHNOLOGICAL FIELD

The present disclosure relates to aerosol delivery devices such as smoking articles, and more particularly to aerosol delivery devices that may utilize electrically generated heat for the production of aerosol (e.g., smoking articles commonly referred to as electronic cigarettes). The smoking articles may be configured to heat an aerosol precursor, which may incorporate materials that may be made or derived from, or otherwise incorporate tobacco, the precursor being capable of forming an inhalable substance for human consumption.

BACKGROUND

Many devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous alternative smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 8,881,737 to Collett et al., U.S. Pat. App. Pub. No. 2013/0255702 to Griffith Jr. et al., U.S. Pat. App. Pub. No. 2014/0000638 to Sebastian et al., U.S. Pat. App. Pub. No. 2014/0096781 to Sears et al., U.S. Pat. App. Pub. No. 2014/0096782 to Ampolini et al., U.S. Pat. App. Pub. No. 2015/0059780 to Davis et al., and U.S. patent application Ser. No. 15/222,615 to Watson et al., filed Jul. 28, 2016, all of which are incorporated herein by reference. See also, for example, the various implementations of products and heating configurations described in the background sections of U.S. Pat. No. 5,388,594 to Counts et al. and U.S. Pat. No. 8,079,371 to Robinson et al., which are incorporated by reference.

However, it may be desirable to provide aerosol delivery devices with improved electronics such as may extend usability of the devices.

BRIEF SUMMARY

The present disclosure relates to aerosol delivery devices, methods of forming such devices, and elements of such devices. The present disclosure thus includes, without limitation, the following example implementations.

Some example implementations provide an aerosol delivery device comprising at least one housing enclosing a reservoir configured to retain an aerosol precursor composition; a heating element; a power source connected to an electrical load that includes the heating element, the power source comprising a rechargeable lithium-ion battery (LiB) and a linear regulator between the power source and load, the linear regulator being configured to maintain a constant voltage level at the electrical load; and a microprocessor configured to operate in an active mode in which the microprocessor is configured to direct power from the power source to the heating element and thereby control the heating element to activate and vaporize components of the aerosol precursor composition.

In some example implementations of the aerosol delivery device of the preceding or any subsequent example implementation, or any combination thereof, the power source further comprises a rechargeable supercapacitor chargeable from the rechargeable LiB, and configured to provide power to the electrical load, the linear regulator being connected to the rechargeable supercapacitor, between the rechargeable supercapacitor and electrical load, and wherein the microprocessor being configured to direct power from the power source to the heating element includes being configured to direct power from the rechargeable supercapacitor to the heating element.

In some example implementations of the aerosol delivery device of any preceding or any subsequent example implementation, or any combination thereof, the linear regulator is configured to maintain the constant voltage level at the electrical load until an output voltage of the rechargeable supercapacitor is below an input voltage range of the linear regulator.

In some example implementations of the aerosol delivery device of any preceding or any subsequent example implementation, or any combination thereof, the power source further comprises a resistor connected to the LiB, between the LiB and the rechargeable supercapacitor.

In some example implementations of the aerosol delivery device of any preceding or any subsequent example implementation, or any combination thereof, the power source further comprises terminals connectable with a charger from which the rechargeable LiB is rechargeable.

In some example implementations of the aerosol delivery device of any preceding or any subsequent example implementation, or any combination thereof, the aerosol delivery device further comprises a motion sensor configured to detect a defined motion of the aerosol delivery device that indicates a vulnerability of the aerosol delivery device, the motion sensor being configured to convert the defined motion to an electrical signal, wherein the microprocessor or motion sensor is configured to recognize the vulnerability and an operation associated with the vulnerability based on the electrical signal, and the microprocessor is configured to control at least one functional element of the aerosol delivery device to perform the operation, which is thereby performed in response to detection of the vulnerability.

In some example implementations of the aerosol delivery device of any preceding or any subsequent example implementation, or any combination thereof, the microprocessor being configured to control at least one functional element includes being configured to shut off the power source, which is thereby shut off in response to detection of the vulnerability of the aerosol delivery device.

In some example implementations of the aerosol delivery device of any preceding or any subsequent example implementation, or any combination thereof, the aerosol precursor composition comprises glycerin and nicotine.

Some example implementations provide a control body coupled or coupleable with a cartridge that is equipped with a heating element and contains an aerosol precursor composition, the control body being coupled or coupleable with the cartridge to form an aerosol delivery device in which the heating element is configured to activate and vaporize components of the aerosol precursor composition, the control body comprising a power source connected to an electrical load that includes the heating element when the control body is coupled with the cartridge, the power source comprising a rechargeable lithium-ion battery (LiB) and a linear regulator between the power source and load, the linear regulator being configured to maintain a constant voltage level at the electrical load; and a microprocessor configured to operate in an active mode in which the control body is coupled with the cartridge, the microprocessor in the active mode being configured to direct power from the power source to the heating element and thereby control the heating element to activate and vaporize components of the aerosol precursor composition.

In some example implementations of the control body of any preceding or any subsequent example implementation, or any combination thereof, the power source further comprises a rechargeable supercapacitor chargeable from the rechargeable LiB, and configured to provide power to the electrical load, the linear regulator being connected to the rechargeable supercapacitor, between the rechargeable supercapacitor and electrical load, and wherein the microprocessor being configured to direct power from the power source to the heating element includes being configured to direct power from the rechargeable supercapacitor to the heating element.

In some example implementations of the control body of any preceding or any subsequent example implementation, or any combination thereof, the linear regulator is configured to maintain the constant voltage level at the electrical load until an output voltage of the rechargeable supercapacitor is below an input voltage range of the linear regulator.

In some example implementations of the control body of any preceding or any subsequent example implementation, or any combination thereof, the power source further comprises a resistor connected to the LiB, between the LiB and the rechargeable supercapacitor.

In some example implementations of the control body of any preceding or any subsequent example implementation, or any combination thereof, the power source further comprises terminals connectable with a charger from which the rechargeable LiB is rechargeable.

In some example implementations of the control body of any preceding or any subsequent example implementation, or any combination thereof, the control body further comprises a motion sensor configured to detect a defined motion of the aerosol delivery device that indicates a vulnerability of the aerosol delivery device, the motion sensor being configured to convert the defined motion to an electrical signal, wherein the microprocessor or motion sensor is configured to recognize the vulnerability and an operation associated with the vulnerability based on the electrical signal, and the microprocessor is configured to control at least one functional element of the aerosol delivery device to perform the operation, which is thereby performed in response to detection of the vulnerability.

In some example implementations of the control body of any preceding or any subsequent example implementation, or any combination thereof, the microprocessor being configured to control at least one functional element includes being configured to shut off the power source, which is thereby shut off in response to detection of the vulnerability of the aerosol delivery device.

In some example implementations of the control body of any preceding or any subsequent example implementation, or any combination thereof, the aerosol precursor composition comprises glycerin and nicotine.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE DRAWING(S)

Having thus described the disclosure in the foregoing general terms, reference will now be made to the accompanying drawings, which are not necessarily drawn to scale, and wherein:

DETAILED DESCRIPTION

Figure 1:
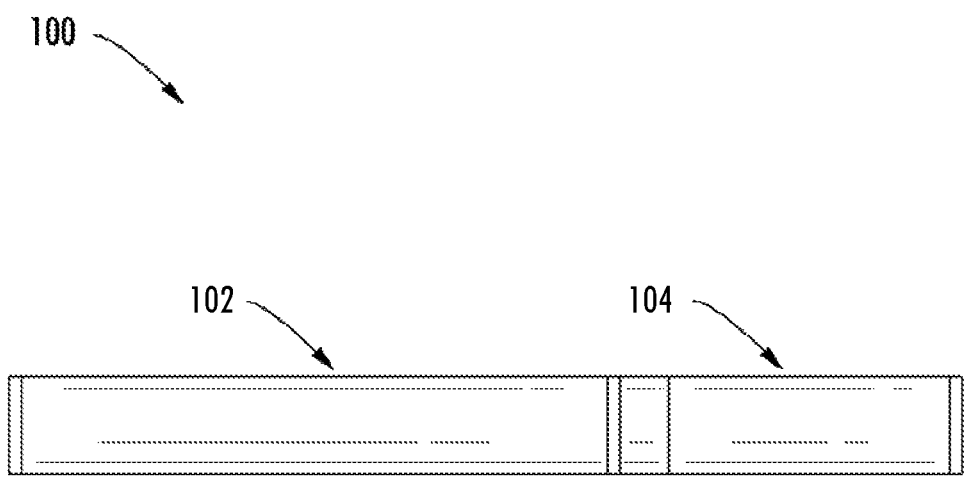
FIG. 1 illustrates a side view of an aerosol delivery device including a cartridge coupled to a control body, according to an example implementation of the present disclosure.

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As described hereinafter, example implementations of the present disclosure relate to aerosol delivery devices. Aerosol delivery devices according to the present disclosure use electrical energy to heat a material (preferably without combusting the material to any significant degree) to form an inhalable substance; and components of such systems have the form of articles most preferably are sufficiently compact to be considered hand-held devices. That is, use of components of preferred aerosol delivery devices does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery devices may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

While the systems are generally described herein in terms of implementations associated with aerosol delivery devices such as so-called "e-cigarettes," it should be understood that the mechanisms, components, features, and methods may be embodied in many different forms and associated with a variety of articles. For example, the description provided herein may be employed in conjunction with implementations of traditional smoking articles (e.g., cigarettes, cigars, pipes, etc.), heat-not-burn cigarettes, and related packaging for any of the products disclosed herein. Accordingly, it should be understood that the description of the mechanisms, components, features, and methods disclosed herein are discussed in terms of implementations relating to aerosol delivery devices by way of example only, and may be embodied and used in various other products and methods.

Aerosol delivery devices of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

In use, aerosol delivery devices of the present disclosure may be subjected to many of the physical actions employed by an individual in using a traditional type of smoking article (e.g., a cigarette, cigar or pipe that is employed by lighting and inhaling tobacco). For example, the user of an aerosol delivery device of the present disclosure can hold that article much like a traditional type of smoking article, draw on one end of that article for inhalation of aerosol produced by that article, take puffs at selected intervals of time, etc.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. In one example, all of the components of the aerosol delivery device are contained within one housing. Alternatively, an aerosol delivery device can comprise two or more housings that are joined and are separable. For example, an aerosol delivery device can possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing cartridge). More specific formats, configurations and arrangements of components within the single housing type of unit or within a multi-piece separable housing type of unit will be evident in light of the further disclosure provided herein. Additionally, various aerosol delivery device designs and component arrangements can be appreciated upon consideration of the commercially available electronic aerosol delivery devices.

Aerosol delivery devices of the present disclosure most preferably comprise some combination of a power source (i.e., an electrical power source), at least one control component (e.g., means for actuating, controlling, regulating and ceasing power for heat generation, such as by controlling electrical current flow the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouthend region or tip for allowing draw upon the aerosol delivery device for aerosol inhalation (e.g., a defined airflow path through the article such that aerosol generated can be withdrawn therefrom upon draw).

Alignment of the components within the aerosol delivery device of the present disclosure can vary. In specific implementations, the aerosol precursor composition can be located near an end of the aerosol delivery device which may be configured to be positioned proximal to the mouth of a user so as to maximize aerosol delivery to the user. Other configurations, however, are not excluded. Generally, the heating element can be positioned sufficiently near the aerosol precursor composition so that heat from the heating element can volatilize the aerosol precursor (as well as one or more flavorants, medicaments, or the like that may likewise be provided for delivery to a user) and form an aerosol for delivery to the user. When the heating element heats the aerosol precursor composition, an aerosol is formed, released, or generated in a physical form suitable for inhalation by a consumer. It should be noted that the foregoing terms are meant to be interchangeable such that reference to release, releasing, releases, or released includes form or generate, forming or generating, forms or generates, and formed or generated. Specifically, an inhalable substance is released in the form of a vapor or aerosol or mixture thereof, wherein such terms are also interchangeably used herein except where otherwise specified.

As noted above, the aerosol delivery device may incorporate a battery or other electrical power source to provide current flow sufficient to provide various functionalities to the aerosol delivery device, such as powering of a heater, powering of control systems, powering of indicators, and the like. The power source can take on various implementations. Preferably, the power source is able to deliver sufficient power to rapidly heat the heating element to provide for aerosol formation and power the aerosol delivery device through use for a desired duration of time. The power source preferably is sized to fit conveniently within the aerosol delivery device so that the aerosol delivery device can be easily handled. Additionally, a preferred power source is of a sufficiently light weight to not detract from a desirable smoking experience.

More specific formats, configurations and arrangements of components within the aerosol delivery devices of the present disclosure will be evident in light of the further disclosure provided hereinafter. Additionally, the selection and arrangement of various aerosol delivery device components can be appreciated upon consideration of commercially-available electronic aerosol delivery devices. Further information regarding formats, configurations and arrangements of components within the aerosol delivery devices of the present disclosure, as well as commercially-available electronic aerosol delivery devices, may be found in U.S. patent application Ser. No. 15/291,771 to Sur et al., filed Oct. 12, 2016, which is incorporated herein by reference.

FIG. 1 illustrates a side view of an aerosol delivery device 100 including a control body 102 and a cartridge 104, according to various example implementations of the present disclosure. In particular, FIG. 1 illustrates the control body and the cartridge coupled to one another. The control body and the cartridge may be detachably aligned in a functioning relationship. Various mechanisms may connect the cartridge to the control body to result in a threaded engagement, a press-fit engagement, an interference fit, a magnetic engagement or the like. The aerosol delivery device may be substantially rod-like, substantially tubular shaped, or substantially cylindrically shaped in some example implementations when the cartridge and the control body are in an assembled configuration. The aerosol delivery device may also be substantially rectangular, rhomboidal or triangular in cross-section, multifaceted shapes, or the like, some of which may lend itself to greater compatibility with a substantially flat or thin-film power source, such as a power source including a flat battery.

The cartridge and control body may include separate, respective housings or outer bodies, which may be formed of any of a number of different materials. The housing may be formed of any suitable, structurally-sound material. In some examples, the housing may be formed of a metal or alloy, such as stainless steel, aluminum or the like. Other suitable materials include various plastics (e.g., polycarbonate), metal-plating over plastic, ceramics and the like.

In some example implementations, one or both of the control body 102 or the cartridge 104 of the aerosol delivery device 100 may be referred to as being disposable or as being reusable. For example, the control body may have a replaceable battery or a rechargeable battery and thus may be combined with any type of recharging technology, including connection to a typical wall outlet, connection to a car charger (i.e., a cigarette lighter receptacle), connection to a computer, such as through a universal serial bus (USB) cable or connector, connection to a photovoltaic cell (sometimes referred to as a solar cell) or solar panel of solar cells, or connection to a RF-to-DC converter. Further, in some example implementations, the cartridge may comprise a single-use cartridge, as disclosed in U.S. Pat. No. 8,910,639 to Chang et al., which is incorporated herein by reference.

Figure 2:
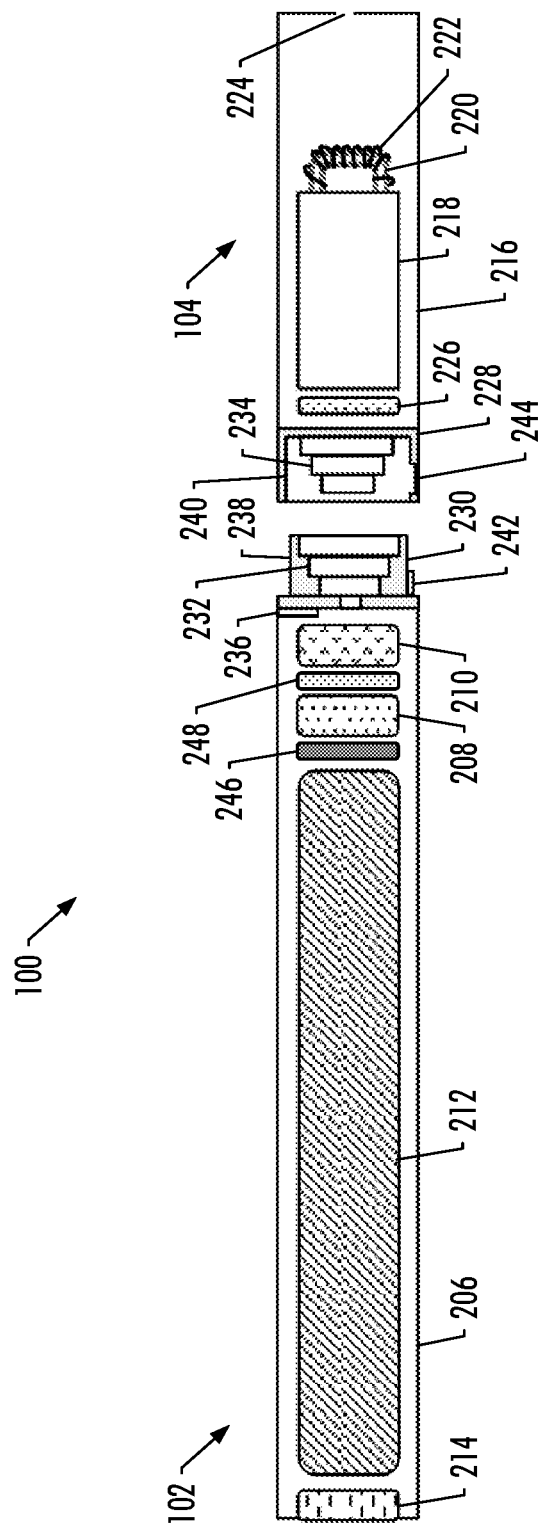
FIG. 2 is a partially cut-away view of the aerosol delivery device according to various example implementations.

FIG. 2 more particularly illustrates the aerosol delivery device 100, in accordance with some example implementations. As seen in the cut-away view illustrated therein, again, the aerosol delivery device can comprise a control body 102 and a cartridge 104 each of which include a number of respective components. The components illustrated in FIG. 2 are representative of the components that may be present in a control body and cartridge and are not intended to limit the scope of components that are encompassed by the present disclosure. As shown, for example, the control body can be formed of a control body shell 206 that can include a control component 208 (e.g., a microprocessor, individually or as part of a microcontroller), a flow sensor 210, a power source 212 and one or more light-emitting diodes (LEDs) 214, quantum dot enabled LEDs or the like, and such components can be variably aligned. The power source may include, for example, a battery (single-use or rechargeable), rechargeable supercapacitor, rechargeable solid-state battery (SSB), rechargeable lithium-ion battery (LiB) or the like, or some combination thereof. Some examples of a suitable power source are provided in U.S. patent application Ser. No. 14/918,926 to Sur et al., filed Oct. 21, 2015, which is incorporated herein by reference. Other examples of a suitable power source are provided in U.S. Pat. App. Pub. No. 2014/0283855 to Hawes et al., U.S. Pat. App. Pub. No. 2014/0014125 to Fernando et al., U.S. Pat. App. Pub. No. 2013/0243410 to Nichols et al., U.S. Pat. App. Pub. No. 2010/0313901 to Fernando et al., and U.S. Pat. App. Pub. No. 2009/0230117 to Fernando et al., all of which are incorporated herein by reference.

The LED 214 may be one example of a suitable visual indicator with which the aerosol delivery device 100 may be equipped. Other indicators such as audio indicators (e.g., speakers), haptic indicators (e.g., vibration motors) or the like can be included in addition to or as an alternative to visual indicators such as the LED, quantum dot enabled LEDs.

The cartridge 104 can be formed of a cartridge shell 216 enclosing a reservoir 218 configured to retain the aerosol precursor composition, and including a heater 222 (sometimes referred to as a heating element). In various configurations, this structure may be referred to as a tank; and accordingly, the terms "cartridge," "tank" and the like may be used interchangeably to refer to a shell or other housing enclosing a reservoir for aerosol precursor composition, and including a heater.

As shown, in some examples, the reservoir 218 may be in fluid communication with a liquid transport element 220 adapted to wick or otherwise transport an aerosol precursor composition stored in the reservoir housing to the heater 222. In some examples, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be a resistive heating element such as a wire coil, micro heater or the like. Example materials from which the heating element may be formed include Kanthal (Fe-CrAl), Nichrome, stainless steel, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as those described herein.

An opening 224 may be present in the cartridge shell 216 (e.g., at the mouthend) to allow for egress of formed aerosol from the cartridge 104.

The cartridge 104 also may include one or more electronic components 226, which may include an integrated circuit, a memory component (e.g., EEPROM, flash memory), a sensor, or the like. The electronic components may be adapted to communicate with the control component 208 and/or with an external device by wired or wireless means. The electronic components may be positioned anywhere within the cartridge or a base 228 thereof.

Although the control component 208 and the flow sensor 210 are illustrated separately, it is understood that various electronic components including the control component and the flow sensor may be combined on an electronic printed circuit board (PCB) that supports and electrically connects the electronic components. Further, the PCB may be positioned horizontally relative the illustration of FIG. 1 in that the PCB can be lengthwise parallel to the central axis of the control body. In some examples, the air flow sensor may comprise its own PCB or other base element to which it can be attached. In some examples, a flexible PCB may be utilized. A flexible PCB may be configured into a variety of shapes, include substantially tubular shapes. In some examples, a flexible PCB may be combined with, layered onto, or form part or all of a heater substrate.

The control body 102 and the cartridge 104 may include components adapted to facilitate a fluid engagement therebetween. As illustrated in FIG. 2, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the heater 222 in the cartridge. Further, the control body shell 206 can include an air intake 236, which may be a notch in the shell where it connects to the coupler that allows for passage of ambient air around the coupler and into the shell where it then passes through the cavity 232 of the coupler and into the cartridge through the projection 234.

A coupler and a base useful according to the present disclosure are described in U.S. Pat. App. Pub. No. 2014/0261495 to Novak et al., which is incorporated herein by reference. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable.

The reservoir 218 illustrated in FIG. 2 can be a container or can be a fibrous reservoir, as presently described. For example, the reservoir can comprise one or more layers of nonwoven fibers substantially formed into the shape of a tube encircling the interior of the cartridge shell 216, in this example. An aerosol precursor composition can be retained in the reservoir. Liquid components, for example, can be sorptively retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as those described herein. In particular, specific combinations of heating members and transport elements as further described below may be incorporated into devices such as those described herein.

In use, when a user draws on the aerosol delivery device 100, airflow is detected by the flow sensor 210, and the heater 222 is activated to vaporize components of the aerosol precursor composition. Drawing upon the mouthend of the aerosol delivery device causes ambient air to enter the air intake 236 and pass through the cavity 232 in the coupler 230 and the central opening in the projection 234 of the base 228. In the cartridge 104, the drawn air combines with the formed vapor to form an aerosol. The aerosol is whisked, aspirated or otherwise drawn away from the heater and out the opening 224 in the mouthend of the aerosol delivery device.

In some examples, the aerosol delivery device 100 may include a number of additional software-controlled functions. For example, the aerosol delivery device may include a power-source protection circuit configured to detect power-source input, loads on the power-source terminals, and charging input. The power-source protection circuit may include short-circuit protection, under-voltage lock out and/or over-voltage charge protection, battery temperature compensation. The aerosol delivery device may also include components for ambient temperature measurement, and its control component 208 may be configured to control at least one functional element to inhibit power-source charging—particularly of any battery—if the ambient temperature is below a certain temperature (e.g., 0° C.) or above a certain temperature (e.g., 45° C.) prior to start of charging or during charging.

Power delivery from the power source 212 may vary over the course of each puff on the device 100 according to a power control mechanism. The device may include a "long puff" safety timer such that in the event that a user or component failure (e.g., flow sensor 210) causes the device to attempt to puff continuously, the control component 208 may control at least one functional element to terminate the puff automatically after some period of time (e.g., four seconds). Further, the time between puffs on the device may be restricted to less than a period of time (e.g., 100 seconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 100 may include a puff tracking algorithm configured for heater lockout once a defined number of puffs has been achieved for an attached cartridge (based on the number of available puffs calculated in light of the e-liquid charge in the cartridge). The aerosol delivery device may include a sleep, standby or low-power mode function whereby power delivery may be automatically cut off after a defined period of non-use. Further safety protection may be provided in that all charge/discharge cycles of the power source 212 may be monitored by the control component 208 over its lifetime. After the power source has attained the equivalent of a predetermined number (e.g., 200) of full discharge and full recharge cycles, it may be declared depleted, and the control component may control at least one functional element to prevent further charging of the power source.

The various components of an aerosol delivery device according to the present disclosure can be chosen from components described in the art and commercially available. Examples of batteries that can be used according to the disclosure are described in U.S. Pat. No. 9,484,155 to Peckerar et al., which is incorporated herein by reference.

The aerosol delivery device 100 can incorporate the sensor 210 or another sensor or detector for control of supply of electric power to the heater 222 when aerosol generation is desired (e.g., upon draw during use). As such, for example, there is provided a manner or method of turning off power to the heater when the aerosol delivery device is not be drawn upon during use, and for turning on power to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference.

The aerosol delivery device 100 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. No. 8,881,737 to Collet et al., U.S. Pat. No. 9,423,152 to Ampolini et al., U.S. Pat. No. 9,439,454 to Fernando et al., and U.S. Pat. App. Pub. No. 2015/0257445 to Henry et al., all of which are incorporated herein by reference.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. Pat. App. Pub. No. 2015/0059780 to Davis et al., and U.S. Pat. App. Pub. No. 2015/0216232 to Bless et al., all of which are incorporated herein by reference. Additionally, various wicking materials, and the configuration and operation of those wicking materials within certain types of electronic cigarettes, are set forth in U.S. Pat. No. 8,910,640 to Sears et al., which is incorporated herein by reference.

The aerosol precursor composition, also referred to as a vapor precursor composition, may comprise a variety of components including, by way of example, a polyhydric alcohol (e.g., glycerin, propylene glycol or a mixture thereof), nicotine, tobacco, tobacco extract and/or flavorants. Representative types of aerosol precursor components and formulations also are set forth and characterized in U.S. Pat. No. 7,217,320 to Robinson et al., U.S. Pat. No. 9,254,002 to Chong et al., U.S. Pat. No. 8,881,737 to Collett et al., U.S. Pat. Pub. No. 2013/0008457 to Zheng et al., U.S. Pat. Pub. No. 2015/0020823 to Lipowicz et al., and U.S. Pat. Pub. No. 2015/0020830 to Koller, as well as PCT Pat. App. Pub. No. WO 2014/182736 to Bowen et al., and U.S. patent application Ser. No. 15/222,615 to Watson et al., filed Jul. 28, 2016, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

Implementations of effervescent materials can be used with the aerosol precursor, and are described, by way of example, in U.S. Pat. App. Pub. No. 2012/0055494 to Hunt et al., which is incorporated herein by reference. Further, the use of effervescent materials is described, for example, in U.S. Pat. No. 4,639,368 to Niazi et al., U.S. Pat. No. 5,178,878 to Wehling et al., U.S. Pat. No. 5,223,264 to Wehling et al., U.S. Pat. No. 6,974,590 to Pather et al., U.S. Pat. No. 7,381,667 to Bergquist et al., U.S. Pat. No. 8,424,541 to Crawford et al., and U.S. Pat. No. 8,627,828 to Strickland et al., as well as U.S. Pat. No. 9,307,787 to Sun et al., U.S. Pat. App. Pub. No. 2010/0018539 to Brinkley et al., and PCT Pat. App. Pub. No. WO 97/06786 to Johnson et al., all of which are incorporated by reference herein. Additional description with respect to implementations of aerosol precursor compositions, including description of tobacco or components derived from tobacco included therein, is provided in U.S. patent application Ser. Nos. 15/216,582 and 15/216,590, each filed Jul. 21, 2016 and each to Davis et al., which are incorporated herein by reference.

Additional representative types of components that yield visual cues or indicators may be employed in the aerosol delivery device 100, such as visual indicators and related components, audio indicators, haptic indicators and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. Pat. No. 9,451,791 to Sears et al., all of which are incorporated herein by reference.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. No. 8,689,804 to Fernando et al., U.S. Pat. App. Pub. No. 2013/0192623 to Tucker et al., U.S. Pat. No. 9,427,022 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. No. 9,220,302 to DePiano et al., all of which are incorporated herein by reference.

As indicated above, the control component 208 includes a number of electronic components, and in some examples may be formed of a PCB. The electronic components may include a microprocessor or processor core, and a memory. In some examples, the control component may include a microcontroller with integrated processor core and memory, and may further include one or more integrated input/output peripherals. In some examples, the control component may be coupled to a communication interface 246 to enable wireless communication with one or more networks, computing devices or other appropriately-enabled devices. Examples of suitable communication interfaces are disclosed in U.S. Pat. App. Pub. No. 2016/0261020 to Marion et al., the content of which is incorporated herein by reference. Another example of a suitable communication interface is the CC3200 single chip wireless microcontroller unit (MCU) from Texas Instruments. And examples of suitable manners according to which the aerosol delivery device may be configured to wirelessly communicate are disclosed in U.S. Pat. App. Pub. No. 2016/0007651 to Ampolini et al., and U.S. Pat. App. Pub. No. 2016/0219933 to Henry, Jr. et al., each of which is incorporated herein by reference.

In accordance with some example implementations, the control component 208 may include or be coupled to a motion sensor 248 configured to detect a defined motion of the aerosol delivery device 100 that indicates a vulnerability of the aerosol delivery device. The motion sensor may be any of a number of sensors that may be configured to detect the defined motion, convert the defined motion to an electrical signal and output the electrical signal. Examples of suitable motion sensors include single or combinations of tilt sensors, single or multi-axis accelerometers, gyroscopes and the like, any one or more of which may be constructed using microelectromechanical systems-based (MEMS) techniques.

The motion sensor 248 may be configured to convert the defined motion to an electrical signal. The control component 208 or motion sensor may be configured to recognize the vulnerability and an operation associated with the vulnerability based on the electrical signal. In some examples, the defined motion detectable by the motion sensor may include vibration, shock or freefall. Consider in particular examples in which the motion sensor is an accelerometer. In these examples, vibration may be detectable by a periodic acceleration of at least a threshold amount. Additionally or alternatively, shock may be detectable by at least a threshold amount of acceleration for less than a threshold period of time, or freefall may be detectable by less than a threshold amount of acceleration for at least a threshold period of time.

The control component may then be configured to control at least one functional element of the aerosol delivery device 100 to perform the operation, which may be thereby performed in response to detection of the vulnerability. For example, the control component may be configured to shut off the power source 212, which may be thereby shut off in response to detection of the vulnerability of the aerosol delivery device. For more information regarding this aspect, see U.S. patent application Ser. No. 14/961,421 to Sur et al., filed Dec. 7, 2015, which is incorporated herein by reference.

Figure 3:
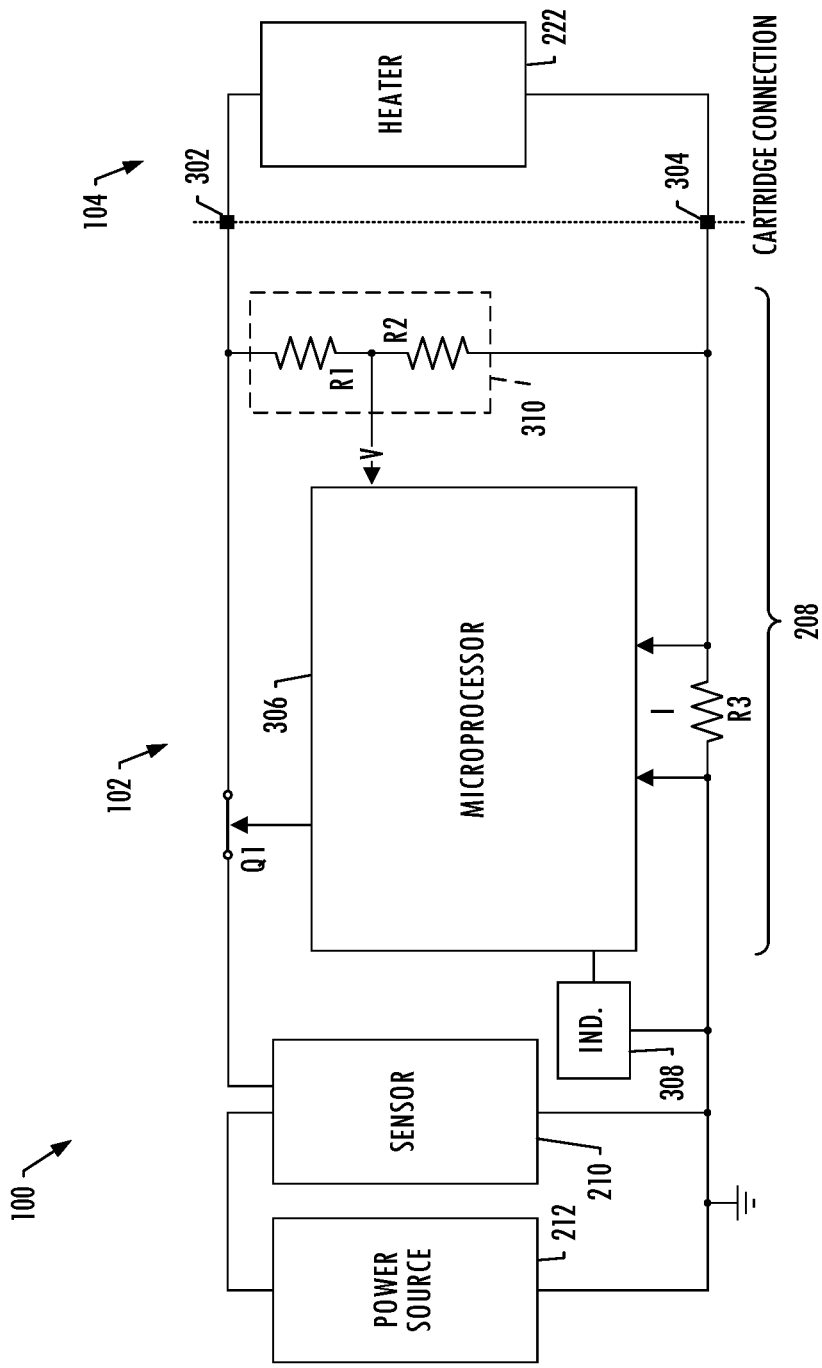
FIG. 3 illustrates various elements of a control body and cartridge of the aerosol delivery device, according to various example implementations.

In accordance with some example implementations, the control component 208 may be configured to control one or more functional elements of the aerosol delivery device 100 in different states of the device. FIG. 3 illustrates the control body 102 coupled with the cartridge 104 in an active mode. As shown, the control body may include positive and negative terminals 302, 304 connectable with corresponding terminals of the heater 222 (heating element). The control component 208 may include a microprocessor 306 and a number of other electrical components, such as resistors, capacitors, switches and the like, which may be coupled with the power source 212 and heater to form an electrical circuit. In some examples, the heater may include a communication terminal for communicating data such as the puff count.

In accordance with example implementations of the present disclosure, the microprocessor 306 may be configured to measure the voltage at the positive terminal 302 and control power to the heater 222 based thereon. In some examples, the microprocessor may also control operation of at least one functional element of the aerosol delivery device 100 based on the voltage at the positive terminal. One example of a suitable functional element may be an indicator 308 such as a visual, audio or haptic indicator.

The microprocessor 306 may operate on the actual voltage at the positive terminal 302, or an analog-to-digital converter (ADC) may be included to convert the actual voltage to a digital equivalent. In some examples, the ADC may be rated for a maximum voltage less than the maximum that may be present at the positive terminal. In these examples, the control component 208 may include a voltage divider 310 configured to reduce the voltage to the microprocessor. As shown, for example, the voltage divider may include resistors R1 and R2, and may be connected to, and positioned between, the positive terminal and microprocessor, referenced to ground. The microprocessor may be configured to measure the voltage at the positive terminal from the voltage divider. In this regard, the voltage divider may include an output connected to the microprocessor and from which the microprocessor may be configured to measure the voltage at the positive terminal.

In examples in which the aerosol delivery device 100 has a housing formed of separable bodies, the aerosol delivery device, and more particularly the control component 102, may be in the standby mode when the control component is uncoupled with the cartridge 104. In examples of either a unitary or separable housing, the aerosol delivery device may be in the standby mode between puffs when the control component is coupled with the cartridge. Similarly, in examples of either a unitary or separable housing, when the user draws on the device and the flow sensor 210 detects airflow, the aerosol delivery device may be placed in the active mode during which power from the power source 212 may be directed through the sensor to power the heater 222 to activate and vaporize components of the aerosol precursor composition. In another example, power from the power source may more directly power the heater without going through the sensor (without the sensor being in-line), although the flow sensor may still detect airflow when the user draws on the device. As indicated above, power delivery from the power source may vary according to a power control mechanism; and in some examples, this power control mechanism may depend on a measured voltage at the positive terminal 302.

In the active mode in which the control body 102 is coupled with the cartridge 104 (with a unitary or separable housing), the microprocessor 306 may be configured to direct power to the heater 222 to activate and vaporize components of the aerosol precursor composition. The voltage at the positive terminal 302 may correspond to a positive heater voltage. The microprocessor may be configured to measure the positive heater voltage, such as from the voltage divider 310, and control the power directed to the heater based thereon.

In some more particular examples, the microprocessor 306 may be configured to direct power from the power source 212 (e.g., directly or through the flow sensor 210) to turn the heater 222 on and commensurately initiate a heating time period. This may include, for example, a switch Q1 between the power source (or in-line flow sensor) and the heater, which the microprocessor may operate in a closed state, as shown in FIG. 3. The microprocessor may then adjust the power directed to the heater based on the voltage at the positive terminal 302, at a periodic rate until expiration of the heating time period.

In some examples, this adjustment of power directed to the heater 222 may include the microprocessor 306 being configured to determine a moving window of measurements of instantaneous actual power directed to the heater, with each measurement of the window of measurements being determined as a product of the positive heater voltage and a current through the heater. This current may be measured in a number of different manners, such as from a current-sense resistor R3. In some examples, the microprocessor may operate on the actual current through the heater, or the control component 208 or microprocessor may include an ADC configured to convert the actual current to a digital equivalent.

The microprocessor 306 may calculate a simple moving average power directed to the heater 222 based on the moving window of measurements of instantaneous actual power, and compare the simple moving average power to a selected power set point associated with the power source 212. The microprocessor may then adjust the power directed to the heater so as to turn the heater off or on at the periodic rate at each instance in which the simple moving average power is respectively above or below the selected power set point. More information regarding aspects of the control component according to example implementations of the present disclosure may be found in the above-cited and incorporated U.S. Pat. App. Pub. No. 2014/0270727 to Ampolini et al.

Figure 4:
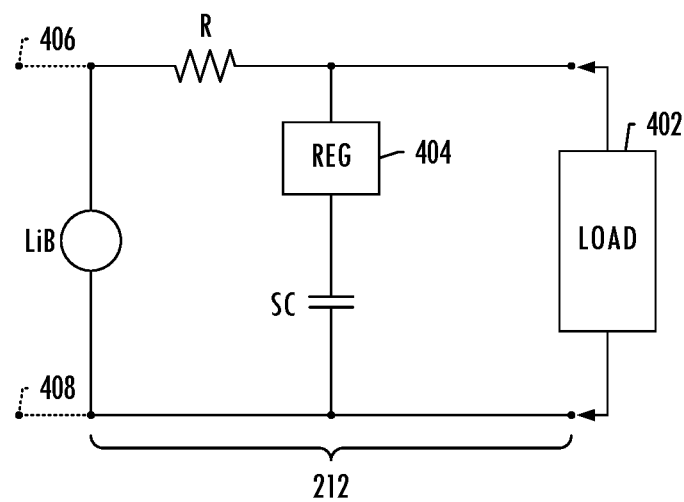
FIG. 4 illustrates a power source for the aerosol delivery device that includes a rechargeable lithium-ion battery (LiB) and linear regulator, according to example implementations.

FIG. 4 illustrates one example of a power source 212 for the aerosol delivery device 100 that includes the rechargeable LiB, according to example implementations of the present disclosure. As shown, the power source is connected to an electrical load 402 that includes the heater 222 (heating element) when the control body 102 is coupled with the cartridge 104. More particularly, the electrical load may include the control component 208 (and its electrical components including the microprocessor 306) and heater, which explained above, may be coupled with the power source to form an electrical circuit. This may additionally include, for example, the flow sensor 210, indicator 308 and the like.

As also shown, in some examples, the power source 212 includes a rechargeable supercapacitor SC chargeable from the rechargeable LiB, and configured to provide power to the electrical load 402. In these examples, microprocessor being configured to direct power from the power source to the heating element includes being configured to direct power from the supercapacitor to the heater. The supercapacitor may smooth fluctuating power from the rechargeable LiB when the rechargeable LiB weakens, and may thereby increase its lifetime and cycle life. The supercapacitor may be any of a number of different types of supercapacitors, such as an electric double-layer capacitor (EDLC), a hybrid capacitor such as a lithium-ion capacitor (LIC), or the like.

In some examples, the power source 212 further includes other components such as a linear regulator 404 and/or a resistor R. As shown, the linear regulator may be connected to the supercapacitor SC, between the supercapacitor and the electrical load 402. The linear regulator may be configured to maintain the constant voltage level at the electrical load until an output voltage of the supercapacitor SC is below an input voltage range of the linear regulator. Examples of a suitable linear regulator include low-dropout (LDO) regulators such as a model 7803 or 7805 LDO. The resistor R may be connected to, and between, the rechargeable LiB and linear regulator. FIG. 4 illustrates the power source including both a linear regulator and resistor, but it should be understood that the power source may include either without the other. The linear regulator may avoid too fast discharge of the supercapacitor SC, and it may facilitate a uniform dissipation of current so that the supercapacitor provides constant power to the electrical load 402. And the resistor may current-limit the charges going to the linear regulator so that they fall within the spec of the linear regulator, which may be beneficial for certain rechargeable LiBs that can dissipate a high discharge current.

In some examples, the power source 212 may further include terminals 406, 408 connectable with a charger from which the rechargeable LiB is rechargeable. As indicated above, the charger may implement any of a number of different types of recharging technology, such as connection to a typical wall outlet, a car charger, a computer (e.g., through USB), a photovoltaic cell or solar panel of solar cells, a RF-to-DC converter or the like.

Reference is briefly made back to examples in which the aerosol delivery device 100 includes the motion sensor 248 and the control component 208 includes the microprocessor 306. In these examples, the microprocessor or motion sensor is configured to recognize the vulnerability and an operation associated with the vulnerability based on the electrical signal. The microprocessor, then, is configured to control at least one functional element of the aerosol delivery device to perform the operation, which is thereby performed in response to detection of the vulnerability. For example, the microprocessor may be configured to shut off the power source, which is thereby shut off in response to detection of the vulnerability of the aerosol delivery device.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-4 or as otherwise described above may be included in an aerosol delivery device according to the present disclosure.

Many modifications and other implementations of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific implementations disclosed, and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:
   at least one housing enclosing a reservoir configured to retain an aerosol precursor composition;
   a heating element;
   a power source connected to an electrical load that includes the heating element, the power source comprising a rechargeable lithium-ion battery (LiB) and a linear regulator between the power source and the electrical load, the linear regulator being configured to maintain a constant voltage level at the electrical load; and
   a microprocessor configured to operate in an active mode in which the microprocessor is configured to direct power from the power source to the heating element and thereby control the heating element to activate and vaporize components of the aerosol precursor composition,
   wherein the power source further comprises:
      a rechargeable supercapacitor chargeable from the rechargeable LiB, and configured to provide power to the electrical load, the linear regulator being connected to the rechargeable supercapacitor, between the rechargeable supercapacitor and the electrical load; and
      a resistor connected to the LiB, between the LiB and the rechargeable supercapacitor, and
   wherein the microprocessor being configured to direct power from the power source to the heating element includes being configured to direct power from the rechargeable supercapacitor to the heating element.

2. The aerosol delivery device of claim 1, wherein the linear regulator is configured to maintain the constant voltage level at the electrical load until an output voltage of the rechargeable supercapacitor is below an input voltage range of the linear regulator.

3. The aerosol delivery device of claim 1, wherein the power source further comprises terminals connectable with a charger from which the rechargeable LiB is rechargeable.

4. An aerosol delivery device comprising:
   at least one housing enclosing a reservoir configured to retain an aerosol precursor composition;
   a heating element;
   a power source connected to an electrical load that includes the heating element, the power source comprising a rechargeable lithium-ion battery (LiB) and a linear regulator between the power source and load, the linear regulator being configured to maintain a constant voltage level at the electrical load;
   a microprocessor configured to operate in an active mode in which the microprocessor is configured to direct power from the power source to the heating element and thereby control the heating element to activate and vaporize components of the aerosol precursor composition; and
   a motion sensor configured to detect a defined motion of the aerosol delivery device that indicates a vulnerability of the aerosol delivery device, the motion sensor being configured to convert the defined motion to an electrical signal,
   wherein the microprocessor or motion sensor is configured to recognize the vulnerability and an operation associated with the vulnerability based on the electrical signal, and the microprocessor is configured to control at least one functional element of the aerosol delivery device to perform the operation, which is thereby performed in response to detection of the vulnerability.

5. The aerosol delivery device of claim 4, wherein the microprocessor being configured to control at least one functional element includes being configured to shut off the power source, which is thereby shut off in response to detection of the vulnerability of the aerosol delivery device.

6. The aerosol delivery device of claim 1, wherein the aerosol precursor composition comprises glycerin and nicotine.

7. A control body coupled or coupleable with a cartridge that is equipped with a heating element and contains an aerosol precursor composition, the control body being coupled or coupleable with the cartridge to form an aerosol delivery device in which the heating element is configured to activate and vaporize components of the aerosol precursor composition, the control body comprising:
   a power source connected to an electrical load that includes the heating element when the control body is coupled with the cartridge, the power source comprising a rechargeable lithium-ion battery (LiB) and a linear regulator between the power source and the electrical load, the linear regulator being configured to maintain a constant voltage level at the electrical load; and
   a microprocessor configured to operate in an active mode in which the control body is coupled with the cartridge, the microprocessor in the active mode being configured to direct power from the power source to the heating element and thereby control the heating element to activate and vaporize components of the aerosol precursor composition,
   wherein the power source further comprises:
      a rechargeable supercapacitor chargeable from the rechargeable LiB, and configured to provide power to the electrical load, the linear regulator being connected to the rechargeable supercapacitor, between the rechargeable supercapacitor and the electrical load; and
      a resistor connected to the LiB, between the LiB and the rechargeable supercapacitor, and
   wherein the microprocessor being configured to direct power from the power source to the heating element includes being configured to direct power from the rechargeable supercapacitor to the heating element.

8. The control body of claim 7, wherein the linear regulator is configured to maintain the constant voltage level at the electrical load until an output voltage of the rechargeable supercapacitor is below an input voltage range of the linear regulator.

9. The control body of claim 7, wherein the power source further comprises terminals connectable with a charger from which the rechargeable LiB is rechargeable.

10. A control body coupled or coupleable with a cartridge that is equipped with a heating element and contains an aerosol precursor composition, the control body being coupled or coupleable with the cartridge to form an aerosol delivery device in which the heating element is configured to activate and vaporize components of the aerosol precursor composition, the control body comprising:
   a power source connected to an electrical load that includes the heating element when the control body is coupled with the cartridge, the power source comprising a rechargeable lithium-ion battery (LiB) and a linear regulator between the power source and load, the linear regulator being configured to maintain a constant voltage level at the electrical load;
   a microprocessor configured to operate in an active mode in which the control body is coupled with the cartridge, the microprocessor in the active mode being configured to direct power from the power source to the heating element and thereby control the heating element to activate and vaporize components of the aerosol precursor composition; and
   a motion sensor configured to detect a defined motion of the aerosol delivery device that indicates a vulnerability of the aerosol delivery device, the motion sensor being configured to convert the defined motion to an electrical signal,
   wherein the microprocessor or motion sensor is configured to recognize the vulnerability and an operation associated with the vulnerability based on the electrical signal, and the microprocessor is configured to control at least one functional element of the aerosol delivery device to perform the operation, which is thereby performed in response to detection of the vulnerability.

11. The control body of claim 10, wherein the microprocessor being configured to control at least one functional element includes being configured to shut off the power source, which is thereby shut off in response to detection of the vulnerability of the aerosol delivery device.

12. The control body of claim 7, wherein the aerosol precursor composition comprises glycerin and nicotine.

* * * * *